United States Patent [19]

Suobank et al.

[11] 4,378,022

[45] Mar. 29, 1983

[54] ENERGY-FREQUENCY-TIME HEART SOUND ANALYSIS

[75] Inventors: David W. Suobank, Pasadena; Earl C. Harrison, South Pasadena; William H. Corcoran, San Gabriel, all of Calif.

[73] Assignee: California Institute of Technology, Pasadena, Calif.

[21] Appl. No.: 225,251

[22] Filed: Jan. 15, 1981

[51] Int. Cl.$^3$ .......................... A61B 5/02; A61B 7/00
[52] U.S. Cl. .................................................. 128/715
[58] Field of Search ................ 128/696, 701, 715, 773

[56] References Cited

U.S. PATENT DOCUMENTS

| | | | |
|---|---|---|---|
| 3,799,147 | 3/1974 | Adolph et al. | 128/715 X |
| 3,878,832 | 4/1975 | Tickner et al. | 128/696 |
| 4,181,134 | 1/1980 | Mason et al. | 128/690 X |
| 4,220,160 | 9/1980 | Kimball et al. | 128/773 X |
| 4,226,248 | 10/1980 | Manoli | 128/773 |

OTHER PUBLICATIONS

Iwata, A. et al, "Algorithm for Detecting the First and the Second Heart Sounds by Spectral Tracking," Med. & Biol. Energy & Computing, Jan. 80, pp. 19-26.
Iwata, A. et al, "Pattern Classification of the Phonocardiogram Using Linear Prediction Analysis," Med. & Biol. Eng. & Comp., Jul. 77, pp. 407-412.
Hearn, T. C. et al, "Temporal & Heart Size Effects on First Heart Sound Spectra," Med. & Biol. Eng. & Comput., Sep. 1979, pp. 563-568.

*Primary Examiner*—Kyle L. Howell
*Assistant Examiner*—Francis J. Jaworski
*Attorney, Agent, or Firm*—Marvin E. Jacobs

[57] ABSTRACT

A method for determining the operability status of heart valves IN VIVO. Accoustical data emanating from a heart valve to be analyzed is gathered. The data are divided into time slices, and the power, energy, and frequency relations for each time slice are calculated. The energy ratio of known peak frequencies is compared between the analysis data as gathered and known energy levels for a properly operating valve. The energy ratio of known frequency bands is also compared between the analysis data as gathered and known energy levels for a properly operating valve. Valve malfunctioning is indicated by the presence of a high change in the power and/or energy ratio at the selected key frequencies and bands.

36 Claims, 12 Drawing Figures

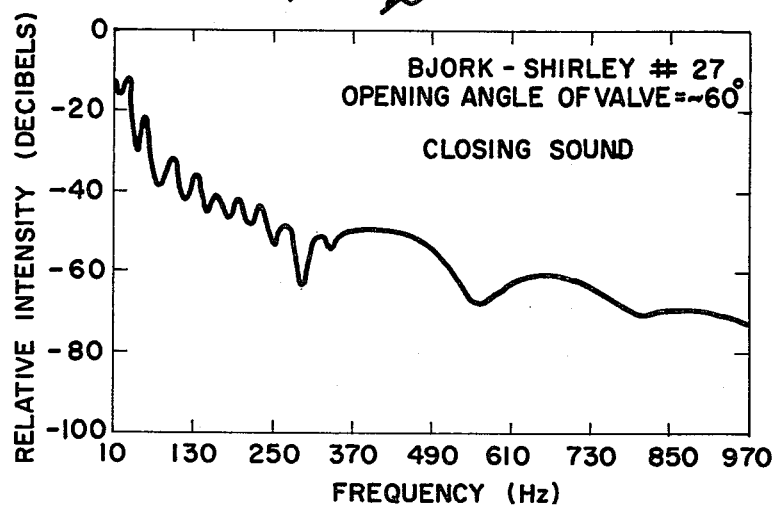
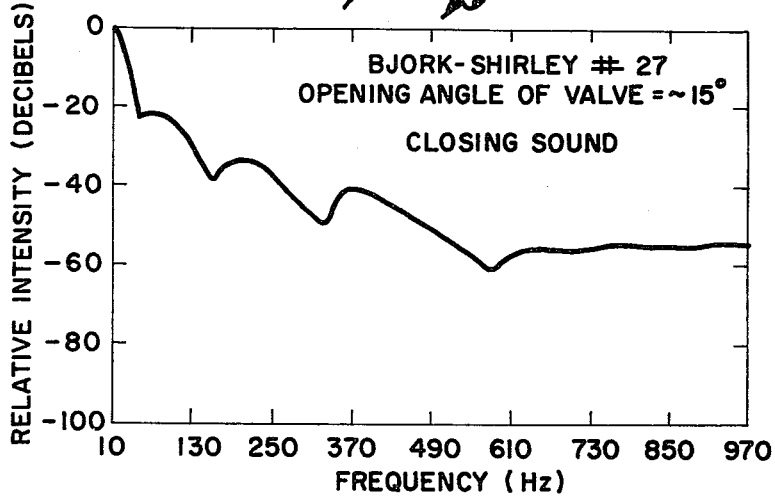
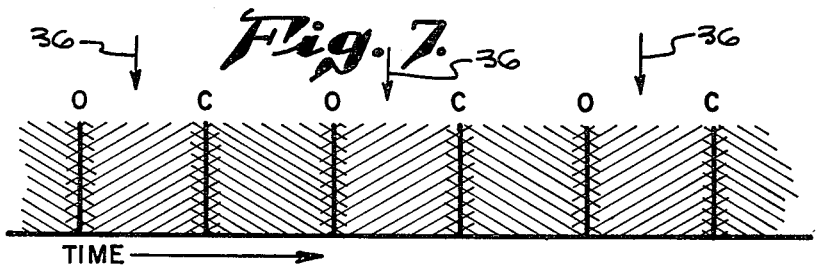

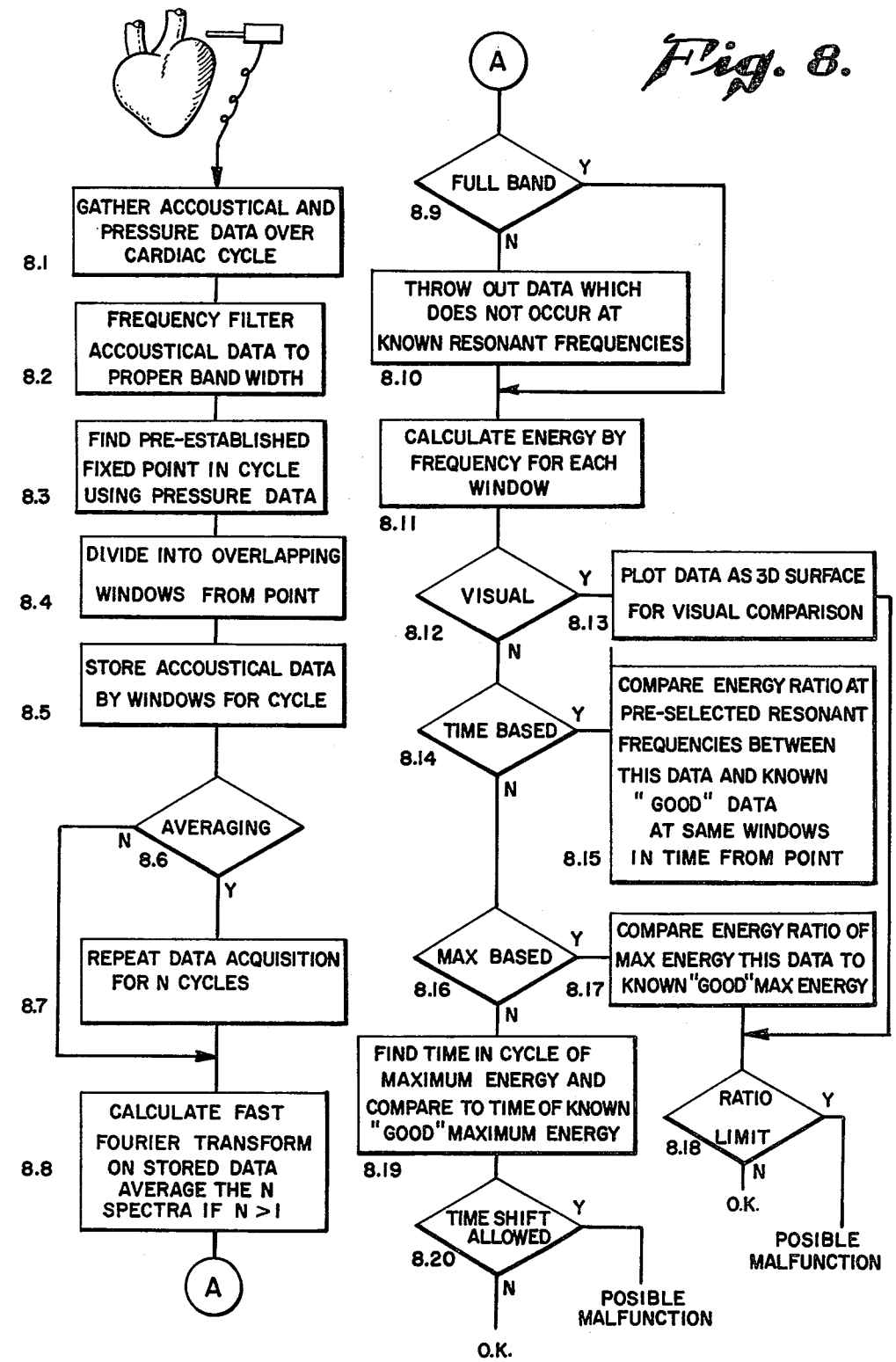

ENERGY-FREQUENCY-TIME HEART SOUND ANALYSIS

BACKGROUND OF THE INVENTION

The present invention relates to methods of in vivo analysis and, in particular, to methods for determining the operability status of heart valves and the like. Heart valve prostheses have been used successfully since 1960. As stated by one author, the decade of 1960 will probably be remembered most in the annals of cardiology as the decade in which cardiac valve replacement became a reality. Of the nearly fifty different heart valves introduced over the last sixteen years, many have been discarded due to their lack of success. Of those remaining, several modifications have been made or are presently being made.

The most commonly used basic types of valves at present are the caged ball, the tilting disc, the caged disc, and tissue or porcine valves. A caged-ball-type valve is shown IN SITU within the blood stream in simplified form in operation in FIG. 1. A tilting-disc type is shown in similar manner in FIG. 2. At present, over ninety thousand prosthetic valves of different designs are used annually throughout the world.

Even after sixteen years of experience, the problems associated with heart-valve prostheses have not been totally eliminated. The most serious problems and complications associated with them are red-cell destruction, thrombosis formation, damage to the endothelial lining of the aortic walls, valve failure due to material fatigue or chemical change, leaks caused by failure of the valve to close properly, infection, and tearing of sewing sutures.

Because of the above mentioned problems, implanted prosthetic valves eventually show some degree of malfunction. If the malfunction of a prosthetic valve is not detected, it could be fatal to the patient. Except for a few valves of recent design, the moving parts of most prosthetic valves contain only plastic materials (specifically non-metallic) such that easily accomplished non-invasive testing cannot be done. Low intensity X-ray analysis through the injection of radiopaque dyes into the heart via catheterization is neither pleasant nor without certain dangers.

Wherefore, it is the object of the present invention to provide a simple non-invasive method of analysis of the operability of heart valves IN VIVO.

SUMMARY

The foregoing objectives have been met by the method of the present invention comprising the steps of disposing of phono-cardiographic transducer in a position to gather time-amplitude acoustical information emanating from the heart valve and adjacent area; gathering the output signal from the transducer over a cardiac cycle; determining the point of a pre-established point in the cardiac cycle within the data; dividing the data of the cardiac cycle into time slices beginning with the pre-established point; calculating the power versus frequency curve for each time slice; comparing the power or energy level associated with the valve being contested at pre-established frequencies within each time slice to corresponding power or energy levels for the same frequency at the same time slice for a known good valve; and, indicating valve malfunction if the power and/or energy ratio of measured data to a known good data is greater than a pre-established amount for over a pre-established threshold number of compared values.

In the ideal state and preferred method of the present invention, the known good data are obtained from the same valve by the same steps performed at a time when it is known that the valve is properly operating. In the case of prosthetic valves, this can be accomplished by gathering such data closely after the implantation thereof.

In the preferred embodiment, the data are digitized at a rate of 2000 samples per second, and only information associated with frequencies between 10 Hz and 1000 Hz is retained. An analog high-pass filter is used to reduce the energy of sound for frequencies less than 100 Hz. Moreover, each cardiac cycle to be analyzed is divided into overlapping windows of 100-ms duration, and the beginning of each successive window occurs at increments of 20 ms.

DESCRIPTION OF THE DRAWINGS

FIG. 5 is a frequency-versus-intensity curve of a normally operating Bjork-Shiley valve in a single-time slice in a closing mode. (unfiltered sound)

FIG. 6 is a frequency-versus-intensity plot for the same time slice for the valve of FIG. 5 in a malfunctioning mode. (unfiltered sound)

FIG. 7 is a drawing depicting the occurrence of data during normal heart operation showing the opening and closing cycles.

FIG. 8 is a flowchart showing the method of the present invention with several testing options.

DESCRIPTION OF THE PREFERRED EMBODIMENT

Figure 1:
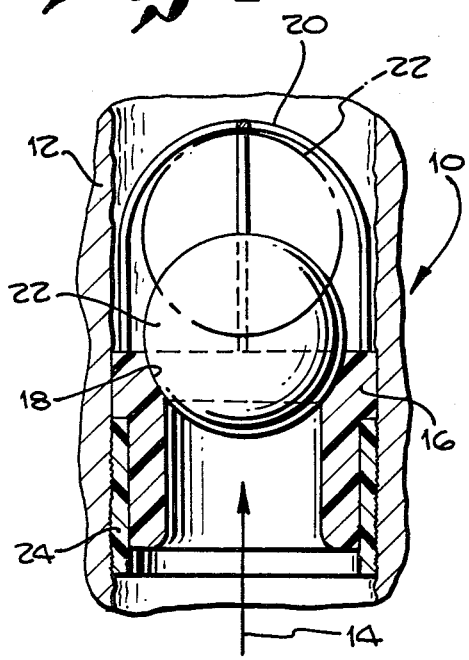
FIG. 1 is a side cut-away elevation through a caged-ball-type prosthetic heart valve in its proper operating condition.

Referring once again to FIG. 1, a caged-ball-type valve is shown and generally indicated as 10. Valve 10 is implanted within a blood vessel such as, the aorta 12 wherein blood flow is in the direction of arrow 14. Valve 10 comprises a cylindrical body portion 16 having a valve seat 18 at the top inner surface thereof. A metallic wire cage 20 is disposed above valve seat 18 and connected to body portion 16. A ball 22 is placed within cage 20. As blood attempts to pass through valve 10 in the proper direction, ball 22 is forced out of valve seat 18 against the top of wire cage 20, whereby the blood can pass up through valve seat 18 and around ball 22 and, therefore, through aorta 12. Any attempt for blood to flow in the opposite direction (i.e. opposite arrow 14) causes ball 22 to be forced into valve seat 18 thereby blocking the flow of blood in the wrong direction through valve 10. Typically, the body portion 16 is provided with a Dacron surface 24.

Figure 3:
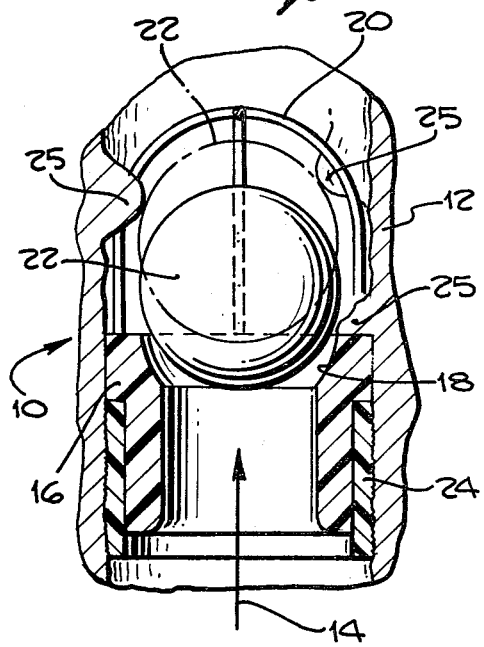
FIG. 3 is a cut-away side elevation of the valve of FIG. 1 in a malfunctioning condition.

Turning to FIG. 3, typically after a period of time the endothelial tissue in the area around valve 10 may grow because of the stimulation of valve 10 as a foreign body. Excess tissue growth can result in the formation of projections 25 which can interfere with both the opening and/or the closing of the valve 10.

Figure 2:
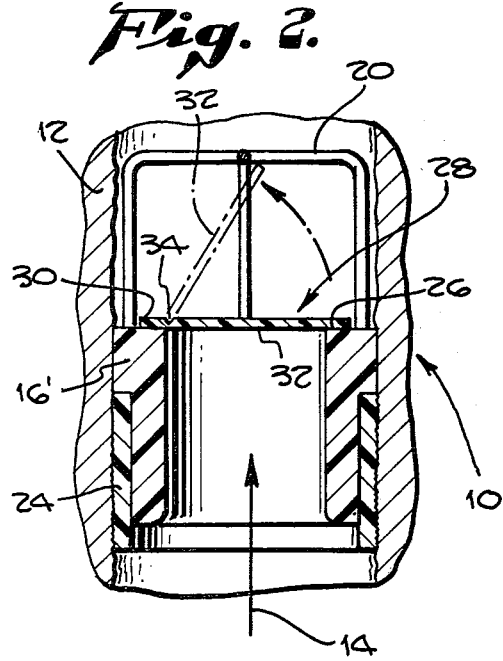
FIG. 2 is a cut-away side elevation through a tilting-disc-type prosthetic heart valve in proper operating condition.
Figure 4:
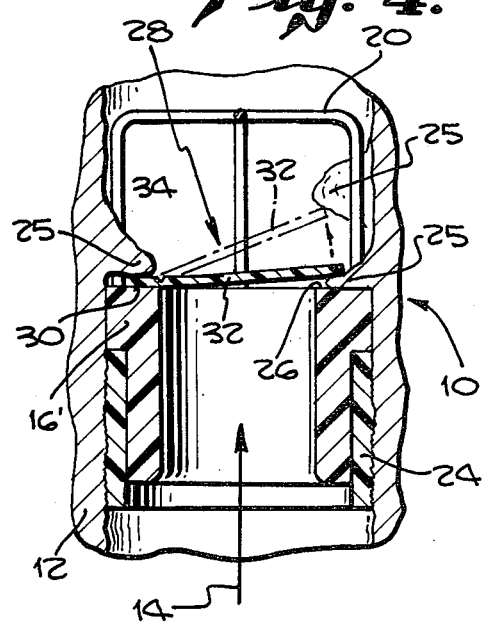
FIG. 4 is a cut-away side elevation of the valve of FIG. 2 in a malfunctioning condition.

Turning now to FIGS. 2 and 4, the same general situation is shown with respect to a tilting disc type valve such as that sold under the name of Bjork-Shiley. In such a valve, the top 26 of the cylindrical body portions 16' forms the valve seat and a tilting disc 28 replaces the ball. Tilting disc 28 has a portion 30 fastened to the top 26 of body portion 16'. The remaining portion 32 of tilting disc 28 is connected to portion 30 by a so-called living hinge 34. Thus, portion 32 is free to rotate about living hinge 34 between the closed position and open (ghosted) positions as shown. Within FIG. 4, these same phenomena of projections 25 as may be caused by the growth of the endothelial tissue of aorta 12 can cause impairment to the operation of the portion 32 by preventing full opening and/or full closure.

In arriving at the present invention, the closing sounds produced by six different aortic prostheses were analyzed for their frequency content by the Fast Fourier Transform (FFT). In addition, the frequency spectrum of the closing sounds of a normal and abnormal aortic prosthesis were compared in order to see if the FFT technique could be used to detect malfunctioning prosthetic valves. All experiments were conducted at California Institute of Technology using its pulse duplicator system. For repeatability and, therefore, more valid comparative results, the experiments were conducted IN VITRO in a simulated environment. The sounds were measured by a Millar phonocatheter (PC-480) which was placed in the aortic flow channel via a wall pressure tap. Therefore, all sounds in the near vicinity of the aortic prosthesis were readily obtained. When the valve is operational, sounds are produced by the operation and vibration of the valve itself as well as by the flow of blood passing through and around the parts of the valve as well as emanating from vibrations in the surrounding tissue itself. Experiments were conducted at a heart rate of 70 beats per minute, an average cardiac output of 5 liters per minute, and a pressure range of 128 mm Hg. The test fluid used in the pulse duplicator was a Polyol V-10 solution (Wyandotte Chemicals) with a viscosity of 3.5 cp at 22° C.

The IN VITRO sounds obtained from the phonocatheter were passed through a heart-sound amplifier (Hewlet Packard model 8813A) and were high-pass filtered at 12 db octave with a cutoff frequency of 100 Hz. The sounds were then recorded, together with the aortic pressure, ventricular pressure, and flow, and the time base on a Hewlett Packard model 3960 FM tape recorder. In actual human testing, this pressure information is most easily obtained by taking the carotid or Korotkoff pressure of the cardiovascular system. The recorded signals were then played back from the tape recorder through, an analog to digital converter at the California Institute of Technology computer center and 30 to 45 second epochs of data were digitized for each experiment. A digitization rate of 2,000 points-per-second was used. The digitized data were stored on a magnetic tape. This tape was then used to generate time plots of the valve sounds on a Calcomp plotter.

Ten to fifteen 100 ms time segments, or windows, containing the closing sounds of the aortic valve were selected. A frequency spectrum of each of these 100-ms time segments was obtained using the Fast Fourier Transform algorithm. Finally, a mean-frequency spectrum for each valve was obtained by averaging the spectra of ten to fifteen closing sounds. This average spectrum was corrected for the 12 db octave filtering, and the resulting spectrum was plotted in graphical form. By analyzing ten to fifteen closing sounds of each valve, any variability introduced by the pulse duplicator was averaged out.

The frequency spectrum obtained showed that in the frequency range of about 10 to 200 Hz there exist some sharp resonant peaks, and beyond that range there are some smooth, wide peaks. The phenomena were observed in the frequency spectrum of a number of different types of valves studied. No resonant peaks were observed above 750 Hz. The reproducibility of the results were verified by performing sound recordings on each valve about two weeks after the first set of experiments and obtaining sound spectra which possessed resonance peaks that were centered within plus or minus 10 Hz of the peaks in the original sound spectrum.

The results of the frequency analysis indicated that with the exception of the Bjork-Shiley valve, the other tested valves have sharp resonant peaks which are quite similar. These six aortic prostheses, however, have characteristic smooth, wide resonant peaks which distinguish each one of them. A mathematical analysis indicated that each of the six frequency spectra obtained were different and distinguishable. That is, early tests indicated that a normal operating prosthetic heart valve had sound characteristics which were reproducible, unique, and identifiable with respect to each type of valve. The next question which presented itself in the evolution of a solution for the stated objectives of the present invention was whether a malfunctioning valve would have sound characteristics which could possibly distinguish it from the normally operating valve.

In order to use the frequency analysis technique as a method to monitor the functional integrity of a prosthetic aortic valve, it was proposed to use the frequency spectrum of the opening and/or closing sound of each normally functioning prosthesis as its own baseline and investigate to see how it changed when pathologically realistic modifications were made to the prosthesis. It was known that the Bjork-Shiley tilting disc aortic prosthesis has been observed to have pathological problems associated with it that impede the opening of the disc as previously discussed with reference to FIGS. 2 and 4. Some of the Bjork-Shiley valves that have been recovered only open to an angle of about 15°, whereas the normal Bjork-Shiley valve opens to an angle of 60°. A previously tested Bjork-Shiley valve was constrained in a pathologically realistic way to open up only to an angle of about 15°, and the sound measurements as previously described were made. It was observed that the intensities of the closing sounds for both experiments were only slightly different and could not be differentiated by the human ear. It was possible to listen to the sounds of the prosthesis via the audiophone output on the heart sound amplifier which was set at a constant gain for both experiments. The frequency spectrum of the closing sounds, however, were very different as shown in FIGS. 5 and 6. The frequency spectrum of the normally functioning Bjork-Shiley valve (FIG. 5) had nine sharp resonant peaks in the frequency range of 25 to 325 Hz, and two smooth, wide peaks at 394 and 665 Hz, respectively. The frequency spectrum of the closing sounds of the malfunctioning valve (FIG. 6) however, had no sharp resonant peaks and had three smooth, wide peaks at 58, 234 and 378 Hz respectively. These results indicated quite clearly that the frequency content of the closing sounds of the normally operating and malfunctioning Bjork-Shiley valve are different and distinguishable.

At present, physicians listen to the intensity of the closing click of the Bjork-Shiley aortic valve in order to judge if the valve is opening completely. The above described in vitro experiment conducted in the pulse duplicator suggested not only that a non-invasive technique for analysis of prosthetic valves to determine malfunctioning was not only probably viable, but, additionally, that the change in sound intensity of a normally functioning valve in a valve that opens to about 15° cannot be detected by the human ear. Thus, if a physician were to use the intensity of the closing click of the Bjork-Shiley aortic valve as a method for detecting any malfunctioning of the valve, he could endanger the life of his patient. Consequently, the evolution of a truly dependable non-invasive method of testing such prosthetic valves appeared not only desirable, but mandatory from a life endangering point of view.

To arrive at a truly viable method for prosthetic-heart-valve testing using acoustical techniques, the operation of the actual cardiovascular system was considered. As shown in symbolic graphic manner in FIG. 7, over a period of time the valves of the heart go through repeated opening and closing cycles separated by periods of stability. The valves of the heart neither open nor close instantaneously, whether it is the actual living heart valve or a prosthetic implant. Thus, while the vertical lines labeled "O" and "C" indicating the opening and closing cycle limits are drawn as lines, as shown by the overlapping cross-hatching, the change in cycle takes a period of time. In the single cross-hatched portion of the time domain of each cycle, the valve and surrounding cardio-vascular tissue as well as the blood flow obtains a stable nature. It is convenient to detect the blood pressure in order to establish a repeating fixed point within each cardiac cycle. For example, the dichrotic notch is a very easily identifiable point within each cardiac cycle. Thus, if data are gathered over a complete cardiac cycle, both as to the acoustical nature and the simultaneous blood pressure associated therewith, a pre-established point within the cardiac cycle can be determined, as symbolized by the arrows 36 in FIG. 7, and from that pre-established point, selected stable portions of the cardiac cycle can be employed as the data base for comparison.

According to the preferred embodiment of the present invention, as finally established, acoustical information in the form of a time-amplitude, analog signal is obtained using standard phono-cardiographic transducers placed either externally or internally near the source of the sound. The unfiltered analog signal is amplified and recorded on FM analogue tape. Analog filtering of the raw data is also done during the recording process. Once the experimental data are stored on tape in files, they are digitized by a standard analog to digital converter at 2,000 points per second and stored on magnetic computer tape. By establishing the location within the data of the pre-established point within the cardiac cycle, the data file of interest is plotted so that a typical cardiac cycle can be chosen along with it starting and ending times. A typical cardiac cycle is of approximately 0.860-second duration. From the total data a series of time slices of data are established. In the preferred embodiment, these time slices are in the form of windows of data in overlapping relationship. Preferably, a window length is chosen of approximately 100 milliseconds, and the time of the beginning of each successive window is incremented 20 milliseconds. Thus, for a 100-millisecond window length and a 20-millisecond increment, it will take 43 windows to cover the entire 860 millisecond cardiac cycle.

Figure 9:
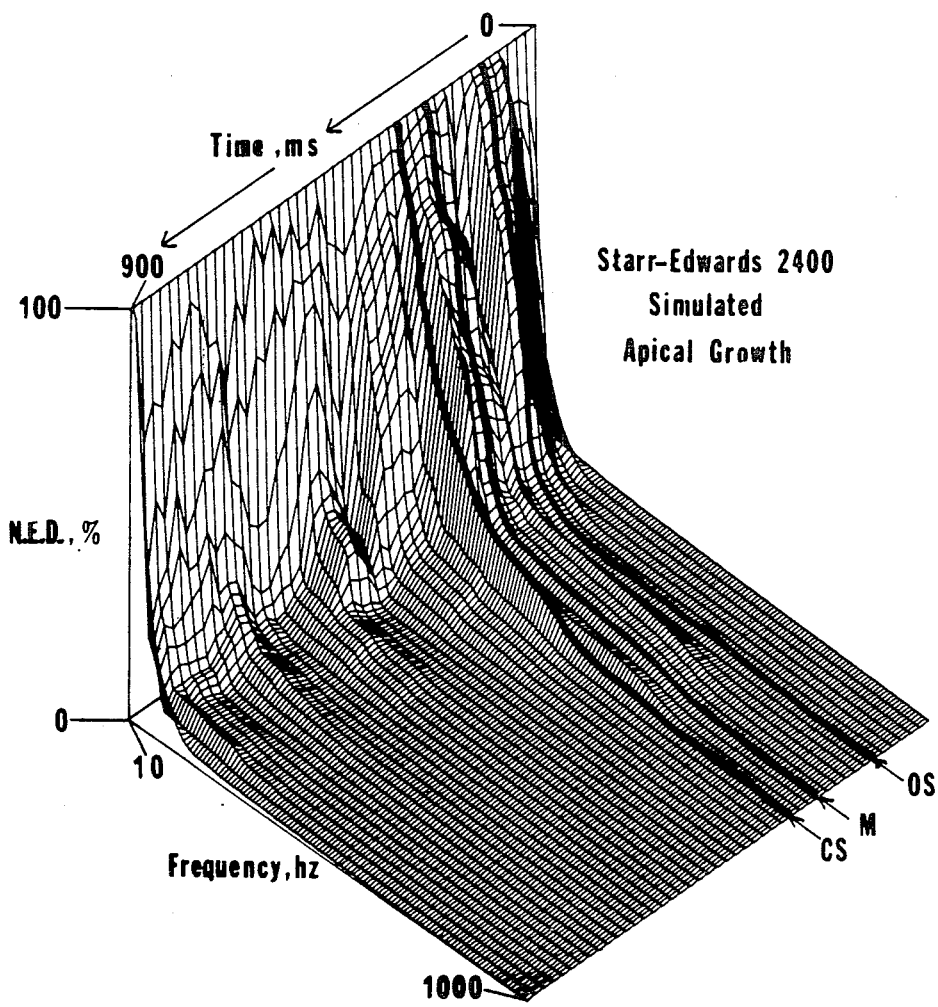
FIG. 9 is a 3D plot of a malfunctioning Starr-Edwards valve.
Figure 10:
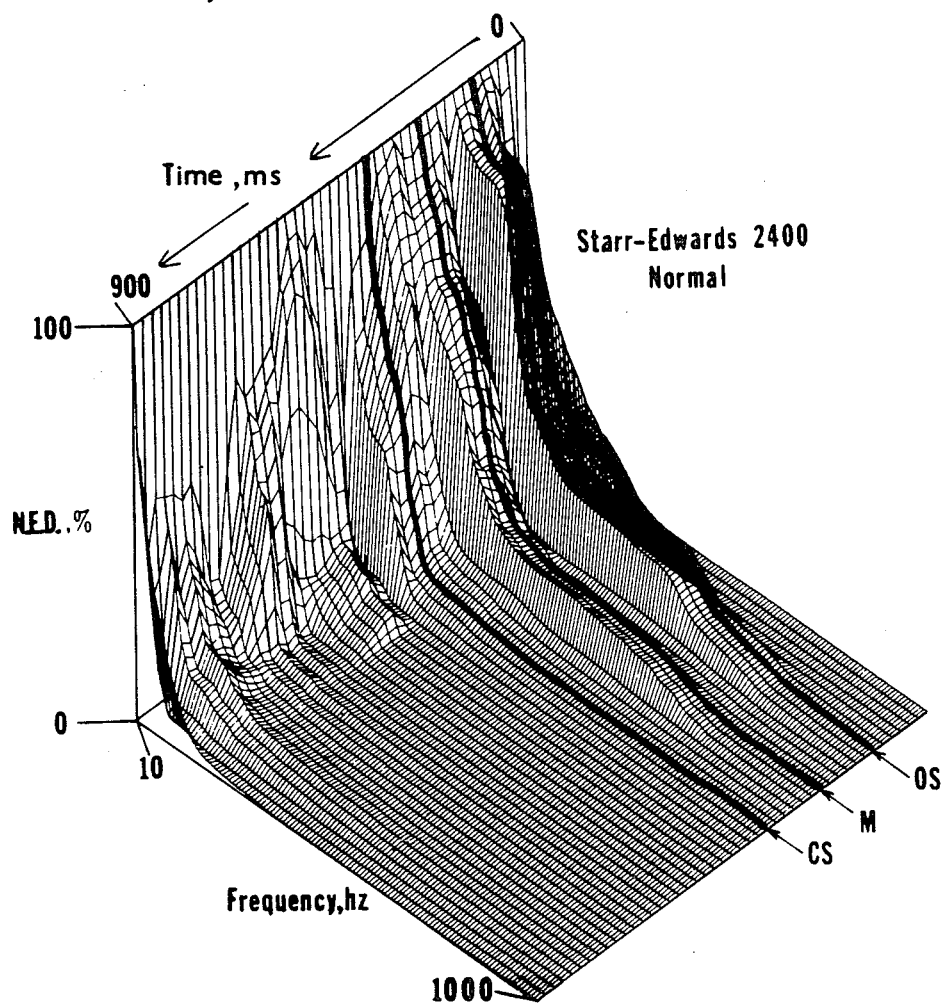
FIG. 10 is a 3D plot of a normally operating Starr-Edwards valve.

While hand calculation of the data would, of course, be possible, modern computer technology makes the calculations and comparisons necessary to implement the technique of the present invention much more practical. For each window, the spectra corresponding to the data line within the time range associated with the window must be calculated. This analysis is most conveniently accomplished by implementing a calculation employing a Fast Fourier algorithm to obtain real and imaginary parts of the complex Fourier coefficients associated with the data within the windows. It is preferred that a modified Hanning window be used to minimize undesirable effects caused by sampling in the time domain. According to one technique as employed and tested, the calculations are performed for each window, and, having obtained the spectra for each of the forty-three windows, a three-dimensional surface plot is generated having time as the third axis associated with the increment of the starting time of successive windows. The 3D surface thus plotted is characteristic of the energy distribution associated with a cardiac system's acoustical state for a specific time range and frequency band width. The foregoing information can be visually checked by a physician or technician for malfunctions. Specifically, the plot of a presently functioning valve is compared against a similar plot for a known properly functioning valve of the same type. Examples of such 3D plots for a normal and a malfunctioning valve are shown in FIGS. 10 and 9, respectively. While specifically developed for detecting malfunctioning prosthetic valves, the present invention appears to also have value in the analysis of living heart valves and, in fact, various other bodily functions. For such latter analysis, a file history of acoustical spectra on individual patients would have to be maintained for later comparison to determine changes therein. While it is possible to have pre-established acoustical spectra on individual prosthetic valves, it is likewise preferred that such data be secured in vivo from the individual patient. That is, following a prosthetic implant is it preferred that an acoustical spectra of "normal" operation be obtained and retained for later comparison during malfunction testing. In addition to the visual comparison possible employing the three-dimensional plot technique, the data can also be compared numerically either manually or by computer.

The information obtained according to the foregoing techniques is valuable for specifically predicting the physical changes occuring in a sound producing system, such as prosthetic heart valves operating within the heart. The energy content of specific valve-related sounds in specific frequency bands has been shown to be a function of the operational state of the valve, specifically the nature of the materials that are in juxtaposition at the time of collision (e.g. the valve poppet and flow orifice). An example of the results of the invention for a specific valve show that the energy ratio between a normal valve and a valve having thrombosis is 3:1, with the specific frequency band 150–300 Hz at the time corresponding to a 100 ms window containing the maximum acoustical energy of the closing sound. That is, the data when employing the present invention can be compared on two bases. According to one technique, specific windows occurring at the same position within a cardiac cycle from the pre-established point within that cycle are compared for known good operational data and the data under test. The total energy ratio across the frequency spectrum can be compared, or, preferably, the energy ratios of those frequencies known to produce resonant peaks in normal operation are compared. An energy ratio higher than a pre-established amount is indicative of a malfunction.

Figure 11:
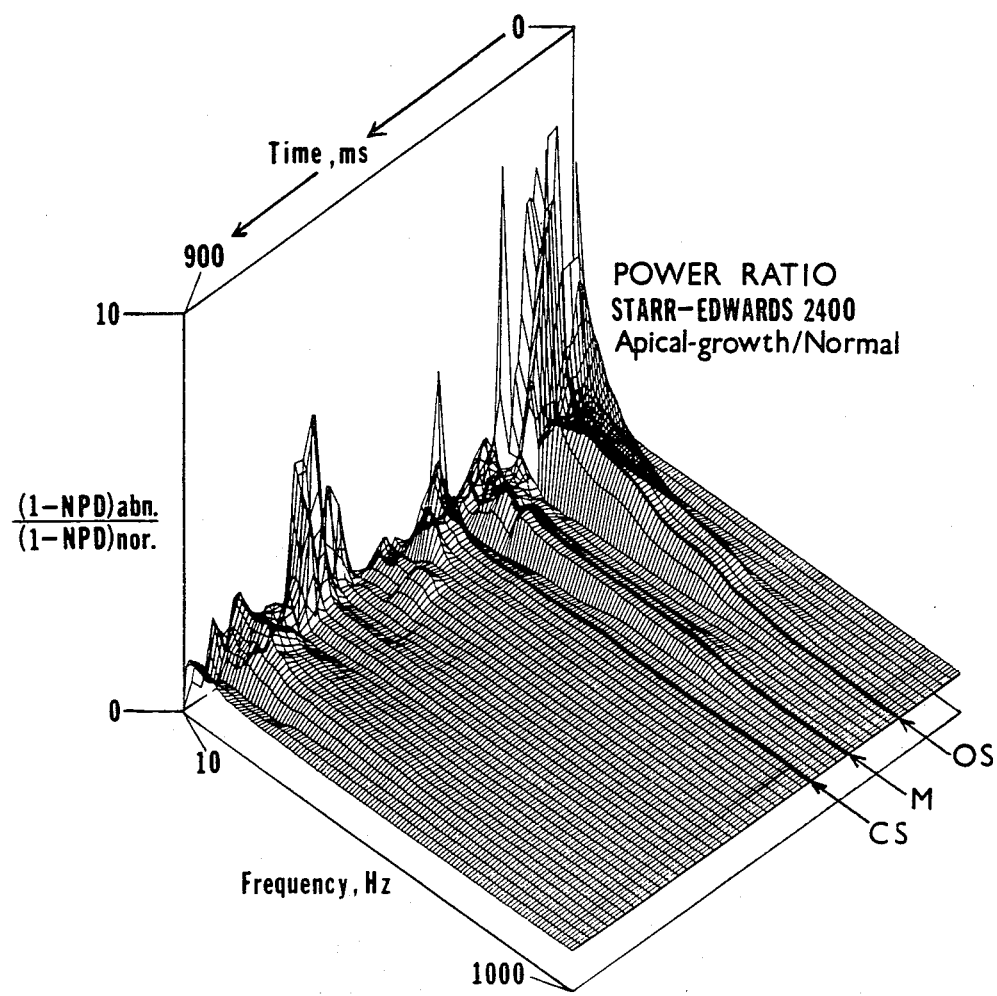
FIG. 11 is a 3D plot of the Power Ratio of the data of FIGS. 9 and 10.
Figure 12:
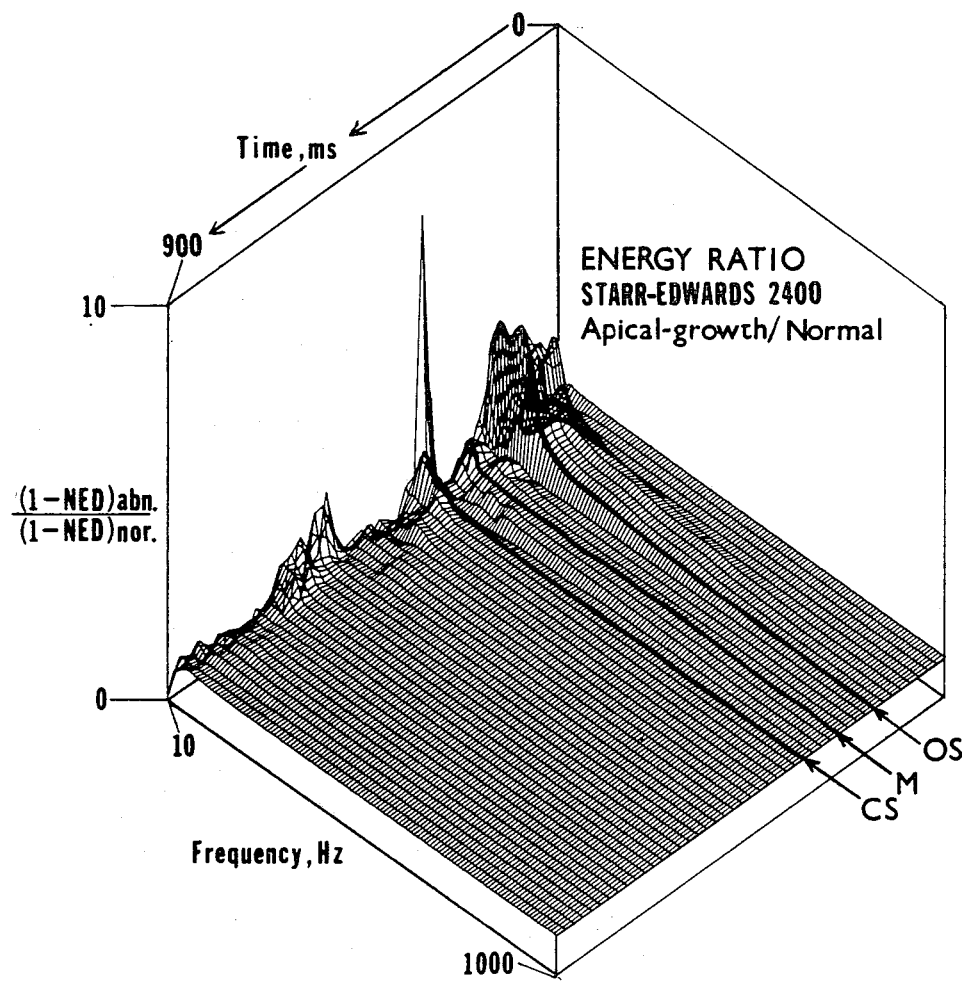
FIG. 12 is a 3D plot of the Energy Ratio of the data of FIGS. 9 and 10.

A particularly useful tool in the analysis of the data is a normalized three-dimensional surface plot of the power or energy ratio. Such plots are shown in FIGS. 11 and 12, respectively, corresponding to the data of FIGS. 9 and 10. If the data were identical, the ratio would produce no points plotted off of the time-frequency plane. Therefore, the three-dimensional nature of the plot quickly shows a variation of the power/energy associated with the abnormal performance as compared to that associated with the normal performance. Thus, the normalized plots such as those of FIGS. 11 and 12 add significantly to understanding the comparison between a normal valve and an abnormal valve.

The normalized energy and power distributions employed and preferred are defined as follows:

Normalized Energy Distribution (N.E.D.) is defined by the relationship:

$$1 - NED(n\Delta f) = \frac{\frac{1}{2}\sum_{k=0}^{n}\left[\frac{[a(k\Delta f)]^2 + [b(k\Delta f)]^2}{kf} + \frac{[a((k+1)\Delta f)]^2 + [b((k+1)\Delta f)]^2}{(k+1)f}\right]}{\frac{1}{2}\sum_{k=0}^{N}\left[\frac{[a(k\Delta f)]^2 + [b(k\Delta f)]^2}{k\Delta f} + \frac{[a((k+1)\Delta f)]^2 + [b((k+1)\Delta f)]^2}{(k+1)\Delta f}\right]}$$

Normalized Power Distribution (N.P.D.) is defined by the analogous relationship:

$$1 - NPD(n\Delta f) \equiv \frac{\frac{1}{2}\sum_{k=0}^{n}[a(k\Delta f)]^2 + [b(k\Delta f)]^2 + [a((k+1)\Delta f)]^2 + [b((k+1)\Delta f)]^2}{\frac{1}{2}\sum_{k=0}^{N}[a(k\Delta f)]^2 + [b(k\Delta f)]^2 + [a((k+1)\Delta f)]^2 + [b((k+1)\Delta f)]^2}$$

for n=0, 1, 2, ..., N
and where, $\Delta f$ is the frequency resolution (9.8 Hz) and $a(\omega)$ and $b(\omega)$ are the real and imaginary part of the complex Fourier coefficient for frequency $\omega$.

Rather than establishing specific window-to-window comparisons on a fixed-time position, one can also search the total data for windows having maximum energy data either across the frequency spectrum or at selected frequencies and compare these maximum data for their energy ratio regardless of the time occurrence within the cardiac cycle. In this latter approach, both the energy ratio and the time-phase shift between the occurrence of this maximum energy data could be indicative of malfunction. That is, a change in the energy of the sound produced would tend to indicate a change in the operation of the valve characteristics as would a delay in the occurence of the maximum energy from its expected time of occurence within the cardiac cycle. Such a delay in time could, for example, indicate that a valve was opening completely but was being impeded in its time of operation by tissue growth which would shortly completely stop full operation.

Turning now to FIG. 8, the logic accomplished by the various options within the preferred embodiment as set forth above is shown schematically in low-chart form. The procedure begins at block 8.1 wherein the acoustical and blood-pressure data are gathered over at least one cardiac cycle. In block 8.2, the acoustical data are frequency filtered to the proper band width. As seen previously, in the typical prosthetic heart valve as tested to date, this filtering would be to reduce the energies of frequencies below 100 Hz and above 1000 Hz. The specific filtering would, of course, be dependent upon the system being checked, particularly the valve design.

Next, the bood-pressure data are checked in box 8.3 to find a pre-established fixed point in the cardiac cycle. The easiest point to establish is, of course, the dichrotic notch which occurs between the systolic and diastolic portions of the heart action as mentioned previously.

In box 8.4, the data are divided into overlapping windows using the pre-established point as a starting point. That is, one cardiac cycle is, by definition, the duration of data existing from the pre-established point to the same pre-established point in the next cycle. Because the cardiac cycle in its pressure response generally behaves according to known, pre-established characteristics, having once found a known point, the entire cycle can be mapped out from beginning to end and the data taken in any sequence desired. In forming the overlapping windows of data, it is preferred, as previously mentioned, to use 100 ms windows at 20 ms intervals with a digitization rate of 2000 Hz.

In box 8.5, the acoustical data by windows is stored for the entire cycle. While not shown, it is inherent that the data be stored in a sequential manner such that its time within the cycle is retained.

In question block 8.6, the logic checks to see if averaging is occurring. By "averaging", it is meant that more than one cardiac cycle is being employed in order to eliminate extraneous or inconsistent data. If averaging is not occurring, box 8.7 is bypassed as shown. If averaging is occurring, in the logic represented by box 8.7 the data-acquisition steps of blocks 8.1 through 8.5 are repeated and the data stored as a replacement for the single-cycle data stored in box 8.5.

In box 8.8, the Fast Fourier Transform is used to calculate the parameters of interest for each cycle of the stored data and averaging of the spectra is performed in the frequency domain. Other methods could be used, of course. The Fast Fourier Transform is preferred in that it provides the necessary information at a much faster rate than possible by other methods. The Fast Fourier Transform and its use, of course, are well known in the art and, per se, form no point of novelty in the present invention.

At question block 8.9, the logic next checks to see if the full band of frequencies are being employed. That is, are all the frequencies within the filtered data are being employed. Typically, only the data associated with the known resonant frequencies for the valve under test are employed. The remaining data are discarded by the logic of box 8.10. The box 8.11, the energy by frequency for each window is calculated. The basic data are, of course, provided by the Fast Fourier Transform calculated in box 8.8 and the logic associated with box 8.11 contemplates merely placing the data in a usable form for the balance of the logic.

In decision blocks 8.12, the logic next checks to see if only a visual presentation of the data is desired. If "yes", the logic of box 8.13 plots the data as a three dimensional surface for visual comparison. While the entire process can be accomplished mechanically, with computer logic, it has been found that an analysis of the data in a three dimensional time-frequency-power plot by one skilled in the cardiac art provides insight and decision making capabilities not possible with the single repetitive logic of a computer. In particular, in the preferred manner of implementation, the known good valve IN SITU is tested according to the preceeding logic and, at this point, its data are plotted for visual analysis. The cardiologist then analyzes the data for the particular patient and stores the responses, known as "good" data, for later comparison when possible malfunction is being checked for the same patient. In this manner, the "good" data for each patient is highly individualized to the patient.

When non-visual presentation is being made, the logic next begins a series of checks to determine which of the various data testing options are to be employed. As the balance of the logic illustrated shows, only one type of testing is implemented. As will be readily recognizable to the those skilled in the art, additional logic of a non-inventive nature could be incorporated to cause the foregoing logic to produce more than one, and even all, of the tests described without the necessity for the entire test being repeated. This logic provides no inventive level to the present invention, and is therefore, omitted for simplicity.

In decision box 8.14, the logic checks to see if the test is to be time based. By time based, the test data are compared to the known "good" data at the same window in time within the cardiac cycle. As stated in box 8.15, if a time based check is selected, the energy ratio at pre-selected resonant frequencies is compared between these data and the known data at the same windows in time from the pre-selected point.

If time-based testing is not selected, the logic next checks to see if maximum based testing is desired in decision box 8.16. If "yes", the logic within box 8.17 searches the data for this valve to find the maximum energy in any window. This value is compared to the maximum energy associated with known "good" data. Whether box 8.15 or box 8.17 logic is employed, the results of the comparison are subjected to decision box 8.18 wherein the ratio of the compared data is compared to an appropriate pre-established limit for the test being conducted. If the ratio between the tested data and the known good data is greater than the pre-established allowable amount, a possible malfunction is indicated while if the ratio is not greater than the limit, the valve is indicated as being performing acceptably. While not specifically indicated, it is preferred that the logic within decision box 8.18 include the further limitation that the ratio be greater than the limit for a pre-established number of points which may be one or greater. Typically, a greater number of points is employed in order to throw out a single piece of spurious data. It has been found that, in practice, it is preferred that the data being compared be taken from windows wherein the valve is not in a transitory state. That is, occuring within the single cross-hatched or "stable" area of FIG. 7.

If max-based testing is not indicated in decision box 8.16, the default-testing procedure of "time in cycle" is accomplished beginning with the logic of box 8.19. This method is the previously discussed case where the logic determines the maximum energy occuring within the cycle and then determines the time within the cycle wherein this maximum energy has occurred. This time is compared to the time within the cycle wherein maximum energy occurs for a known "good" valve. In decision logic 8.20 which follows, possible malfunction is indicated if the time shift between the occurrence of the two maximum energies is greater than the allowed amount, and probable valve proper functioning is indicated if the time shift is less than the maximum amount allowed.

With particular reference to the question of data filtering in the present invention, the preferred method of digitizing the data limits the analysis to the broad frequency band of 10–100 Hz. If analog filtering is desired, this can be done. In that case, the preferred method is to employ a filter having a 12 db/octave slope and a 100 Hz lower cutoff frequency. This causes the reduction (but not elimination) of the acoustical energy between 10–100 Hz while leaving the energy in the band 100–1000 Hz unchanged. Although the energy in the 10–100 Hz band is filtered, the residual energies are still of interest since it cannot be totally eliminated. Thus, the results are plotted for the total band of 10–1000 Hz.

It should be understood that power or energy can be measured and compared in accomplishing the objectives of the present invention. Thus, either or both can be employed. In the foregoing description and the claims which follow, the term "power" is usually employed for convenience and simplicity. Whenever "power" or "energy" alone is encountered, the broader "power and/or energy" is implied and considered to be within the scope of the description and claims of the present invention.

Wherefore, having thus described our invention, we claim:

1. The method of determining the operability status of a heart valve in vivo comprising the steps of:
   (a) disposing a phonocardiographic transducer in a positon to gather time-amplitude-acoustical information emanating from the heart valve and adjacent areas;
   (b) gathering the output signal from the transducer from a cardiac cycle;
   (c) determining the location of a pre-established point in the cardiac cycle within the data;
   (d) dividing the data of the cardiac cycle into time slices beginning with the pre-established point;
   (e) calculating the power v. frequency curve for each time slice;

(f) comparing the power level associated with the valve being tested at pre-established frequencies within each time slice to corresponding power levels for the same frequencies at the same time slice for a known good valve; and, (g) indicating valve malfunction if the power ratio of measured data to known good data is greater than a pre-established amount over a pre-established threshold number of compared values.

2. The method of claim 1 wherein:

the power ratio is a Normalized Power Distribution (NPD) defined by the relationship:

$$1 - NPD(n\Delta f) = \frac{\frac{1}{2}\sum_{k=0}^{n}[a(k\Delta f)]^2 + [b(k\Delta f)]^2 + [a((k+1)\Delta f)]^2 + [b((k+1)\Delta f)]^2}{\frac{1}{2}\sum_{k=0}^{N}[a(k\Delta f)]^2 + [b(k\Delta f)]^2 + [a((k+1)\Delta f)]^2 + [b((k+1)\Delta f)]^2}$$

for $n = 0, 1, 2, \ldots, N$ and where, $\Delta f$ is the frequency resolution (9.8 Hz) and $a(\omega)$ and $b(\omega)$ are the real and imaginary part of the complex Fourier coefficient for frequency $\omega$.

3. The method of claim 1 wherein:

the known good data are obtained from the same valve from steps (a) through (e) of claim 1 performed at a time when the valve is known to be properly operating.

4. The method of claim 1 or claim 3 wherein:

step (b) of gathering the output signal includes filtering the signal to remove data associated with frequencies below 100 Hz and above 1000 Hz.

5. The method of claim 1 or claim 4 wherein said step (d) of dividing the data into time slices comprises:

dividing the data into overlapping time windows having a length of duration longer than the increment between windows.

6. The method of claim 5 wherein:

each window is about 100 ms in duration, and the windows are taken at 20 ms increments.

7. The method of claim 1 or claim 3 wherein said step (c) of determining the location of a pre-established point in the cardiac cycle within the data includes the steps of:

(c1) gathering simultaneous blood-pressure data with said acoustical data;

(c2) storing said pressure data in association with said acoustical data as an identifier thereof;

(c3) searching said pressure data for a pre-established point in the cardiac cycle identifiable by its pressure characteristics; and (c4) using the acoustical data associated with said pressure identifiable point in the cardiac cycle as a starting point for step (d).

8. The method of determining the operability status of a heart valve in vivo comprising the steps of:

(a) gathering simultaneously and retaining time-amplitude acoustical information emanating from the heart valve and adjacent area as well as the carotid or Korotkoff pressure within the cardiovascular system as produced by the heart for a cardiac cycle;

(b) searching the retained pressure data for a pre-established point within the cardiac cycle;

(c) using the pre-established point within the data found in step (b) as a starting point and dividing the acoustical data into a series of overlapped data windows for one cardial cycle wherein the duration of each window is longer than the increment between windows;

(d) calculating the power v. frequency curve for each window;

(e) comparing the power level associated with the valve being tested at pre-established known resonant frequencies to the power level at the same frequencies for the same windows in the cardiac cycle for a known good valve; and, (f) indicating valve malfunction if the ratio of the compared power levels is greater than a pre-established amount for greater than a pre-established number of values.

9. The method of claim 8 wherein:

the power ratio is a Normalized Power Distribution (NPD) defined by the relationship:

$$1 - NPD(n\Delta f) = \frac{\frac{1}{2}\sum_{k=0}^{n}[[a(k\Delta f)]^2 + [b(k\Delta f)]^2 + [a((k+1)\Delta f)]^2 + [b((k+1)\Delta f)]^2]}{\frac{1}{2}\sum_{k=0}^{N}[[a(k\Delta f)]^2 + [b(k\Delta f)]^2 + [a((k+1)\Delta f)]^2 + [b((k+1)\Delta f)]^2]}$$

for $n = 0, 1, 2, \ldots, N$ and where, $\Delta f$ is the frequency resolution (9.8 Hz) and $a(\omega)$ and $b(\omega)$ are the real and imaginary part, respectively, of the complex Fourier coefficient for frequency $\omega$.

10. The method of claim 8 wherein:

the known good data are obtained from the same valve by steps (a) through (e) of claim 8 performed at a time when the valve is known to be properly operating.

11. The method of claim 8 or claim 10 wherein:

step (b) of gathering the output signal includes filtering the signal to remove data associated with frequencies below 100 Hz. and above 1000 Hz.

12. The method of claim 8 wherein:

each window is about 100 ms in duration and the windows are taken at 20 ms increments.

13. The method of claim 8 wherein:

only data associated with windows wherein the valve is in a non-transition state between open and closed is employed for step (e) of comparing.

14. The method of determining the operability status of a heart valve in vivo comprising the steps of:

(a) gathering simultaneously and retaining time-amplitude acoustical information emanating from the heart valve and adjacent area as well as the carotid or Korotkoff pressure within the cardiovascular system as produced by the heart for one cardiac cycle;

(b) searching the retained pressure data for a pre-established point within the cardiac cycle;

(c) using the pre-established point within the data found in step (b) as a starting point and dividing the acoustical data into a series of overlapped data windows for one cardiac cycle wherein the duration of each window is longer than the increment between windows;

(d) calculating the power v. frequency curve for each window;

(e) finding the maximum power level associated with the valve being tested at pre-established frequencies during the cardiac cycle;

(f) comparing the maximum power level for the valve being tested to the maximum power for a known good valve; and, (g) indicating valve malfunction if the ratio of the compared maximum power levels is greater than a pre-established amount.

15. The method of claim 14 wherein:
the power ratio is a Normalized Power Distribution (NPD) defined by the relationship:

$$1 - NPD(n\Delta f) \equiv \frac{\frac{1}{2} \sum_{k=0}^{n} [[a(k\Delta f)]^2 + [b(k\Delta f)]^2 + [a((k+1)\Delta f)]^2 + [b((k+1)\Delta f)]^2]}{\frac{1}{2} \sum_{k=0}^{N} [[a(k\Delta f)]^2 + [b(k\Delta f)]^2 + [a((k+1)\Delta f)]^2 + [b((k+1)\Delta f)]^2]}$$

for $n = 0, 1, 2, \ldots, N$ and where, $\Delta f$ is the frequency resolution (9.8 Hz) and $a(\omega)$ and $b(\omega)$ are the real and imaginary part of the complex Fourier coefficient for frequency $\omega$.

16. The method of claim 14 wherein:
the known good data are obtained from the same valve from steps (a) through (e) of claim 14 performed at a time when the valve is known to be operating properly.

17. The method of claim 14 or claim 16 wherein:
step (b) of gathering the output signal includes filtering the signal to remove data associated with frequencies below 100 Hz and above 1000 Hz.

18. The method of claim 14 wherein:
each window is about 100 ms in duration and the windows are taken at 20 ms increments.

19. The method of determining the operability status of a heart valve IN VIVO comprising the steps of:

(a) disposing a phonocardiographic transducer in a positon to gather time-amplitude-acoustical information emanating from the heart valve and adjacent areas;

(b) gathering the output signal from the transducer from a cardiac cycle;

(c) determining the location of a pre-established point in the cardiac cycle within the data;

(d) dividing the data of the cardiac cycle into time slices beginning with the pre-established point;

(e) calculating the energy v. frequency curve for each time slice;

(f) comparing the energy level associated with the valve being tested at pre-established frequencies within each time slice to corresponding energy levels for the same frequencies at the same time slice for a known good valve; and, (g) indicating valve malfunction if the energy ratio of measured data to known good data is greater than a pre-established amount over a pre-established threshold number of compared values.

20. The method of claim 19 wherein:
the energy ratio is a Normalized Energy Distribution (NED) defined by the relationship:

$$1 - NED(n\Delta f) \equiv \frac{\frac{1}{2} \sum_{k=0}^{n} \left[ \frac{[a(k\Delta f)]^2 + [b(k\Delta f)]^2}{k\Delta f} + \frac{[a((k+1)\Delta f)]^2 + [b((k+1)\Delta f)]^2}{(k+1)\Delta f} \right]}{\frac{1}{2} \sum_{k=0}^{N} \left[ \frac{[a(k\Delta f)]^2 + [b(k\Delta f)]^2}{k\Delta f} + \frac{[a((k+1)\Delta f)]^2 + [b((k+1)\Delta f)]^2}{(k+1)\Delta f} \right]}$$

for $n = 0, 1, 2, \ldots, N$ and where, $\Delta f$ is the frequency resolution (9.8 Hz) and $a(\omega)$ and $b(\omega)$ are the real and imaginary part of the complex Fourier coefficient for frequency $\omega$.

21. The method of claim 19 wherein:
the known good data are obtained from the same valve from steps (a) through (e) of claim 19 performed at a time when the valve is known to be properly operating.

22. The method of claim 19 or claim 21 wherein:
step (b) of gathering the output signal includes filtering the signal to remove data associated with frequencies below 100 Hz and above 1000 Hz.

23. The method of claim 19 or claim 22 wherein said step (d) of dividing the data into time slices comprises:
dividing the data into overlapping time windows having a length of duration longer than the increment between windows.

24. The method of claim 23 wherein:
each window is about 100 ms in duration, and the windows are taken at 20 ms increments.

25. The method of claim 19 or claim 21 wherein said step (c) of determining the location of a pre-established point in the cardiac cycle within the data includes the steps of:

(c1) gathering simultaneous blood-pressure data with said acoustical data;

(c2) storing said pressure data in accordance with said acoustical data as an identifier thereof;

(c3) searching said pressure data for a pre-established point in the cardiac cycle identifiable by its pressure characteristics; and (c4) using the acoustical data associated with said pressure identifiable point in the cardiac cycle as a starting point for step (d).

26. The method of determining the operability status of a heart valve in vivo comprising the steps of:

(a) gathering simultaneously and retaining time-amplitude acoustical information emanating from the heart valve and adjacent area as well as the carotid or Korotkoff pressure within the cardiovascular system as produced by the heart for a cardiac cycle;

(b) searching the retained pressure data for a pre-established point within the cardiac cycle;

(c) using the pre-established point within the data found in step (b) as a starting point and dividing the acoustical data into a series of overlapped data windows for one cardial cycle wherein the duration of each window is longer than the increment between windows;
(d) calculating the energy v. frequency curve for each window;
(e) comparing the energy level associated with the valve being tested at pre-established known resonant frequencies to the energy level at the same frequencies for the same windows in the cardiac cycle for a known good valve; and,
(f) indicating valve malfunction if the ratio of the compared energy levels is greater than a pre-established amount for greater than a pre-established number of values.

27. The method of claim 26 wherein:
the energy ratio is a Normalized Energy Distribution (NED) defined by the relationship:

$$1 - NED(n\Delta f) \equiv \frac{\frac{1}{2}\sum_{k=0}^{n}\left[\frac{[a(k\Delta f)]^2 + [b(k\Delta f)]^2}{k\Delta f} + \frac{[a((k+1)\Delta f)]^2 + [b((k+1)\Delta f)]^2}{(k+1)\Delta f}\right]}{\frac{1}{2}\sum_{k=0}^{N}\left[\frac{[a(k\Delta f)]^2 + [b(k\Delta f)]^2}{k\Delta f} + \frac{[a((k+1)\Delta f)]^2 + [b((k+1)\Delta f)]^2}{(k+1)\Delta f}\right]}$$

for n = 0, 1, 2, ..., N
and where, $\Delta f$ is the frequency resolution (9.8 Hz) and $a(\omega)$ and $b(\omega)$ are the real and imaginary part of the complex Fourier coefficient for frequency $\omega$.

28. The method of claim 26 wherein:
the known good data are obtained from the same valve by steps (a) through (e) of claim 26 performed at a time when the valve is known to be properly operating.

29. The method of claim 26 or claim 28 wherein:
step (b) of gathering the output signal includes filtering the signal to remove data associated with frequencies below 100 Hz. and above 1000 Hz.

30. The method of claim 26 wherein:
each window is about 100 ms in duration and the windows are taken at 20 ms increments.

31. The method of claim 26 wherein:
only data associated with windows wherein the valve is in a non-transition state between open and closed is employed for step (e) of comparing.

32. The method of determining the operability status of a heart valve IN VIVO comprising the steps of:
(a) gathering simultaneously and retaining time-amplitude acoustical information emanating from the heart valve and adjacent area as well as the carotid or Korotkoff pressure within the cardiovascular system as produced by the heart for one cardiac cycle;
(b) searching the retained pressure data for a pre-established point within the cardiac cycle;
(c) using the pre-established point within the data found in step (b) as a starting point and dividing the acoustical data into a series of overlapped data windows for one cardiac cycle wherein the duration of each window is longer than the increment between windows;
(d) calculating the energy v. frequency curve for each window;
(e) finding the maximum energy level associated with the valve being tested at pre-established frequencies during the cardiac cycle;
(f) comparing the maximum energy level for the valve being tested to the maximum energy for a known good valve; and,
(g) indicating valve malfunction if the ratio of the compared maximum power levels is greater than a pre-established amount.

33. The method of claim 32 wherein:
the energy ratio is a Normalized Energy Distribution (NED) defined by the relationship:

$$1 - NED(n\Delta f) \equiv \frac{\frac{1}{2}\sum_{k=0}^{n}\left[\frac{[a(k\Delta f)]^2 + [b(k\Delta f)]^2}{k\Delta f} + \frac{[a((k+1)\Delta f)]^2 + [b((k+1)\Delta f)]^2}{(k+1)\Delta f}\right]}{\frac{1}{2}\sum_{k=0}^{N}\left[\frac{[a(k\Delta f)]^2 + [b(k\Delta f)]^2}{k\Delta f} + \frac{[a((k+1)\Delta f)]^2 + [b((k+1)\Delta f)]^2}{(k+1)\Delta f}\right]}$$

for n = 0, 1, 2, ..., N
and where, $\Delta f$ is the frequency resolution (9.8 Hz) and $a(\omega)$ and $b(\omega)$ are the real and imaginary part of the complex Fourier coefficient for frequency $\omega$.

34. The method of claim 32 wherein:
the known good data are obtained from the same valve from steps (a) through (e) of claim 32 performed at a time when the valve is known to be operating properly.

35. The method of claim 32 or claim 34 wherein:
step (b) of gathering the output signal includes filtering the signal to remove data associated with frequencies below 100 Hz and above 1000 Hz.

36. The method of claim 32 wherein:
each window is about 100 ms in duration and the windows are taken at 20 ms increments.

* * * * *

UNITED STATES PATENT AND TRADEMARK OFFICE
CERTIFICATE OF CORRECTION

PATENT NO. : 4,378,022
DATED : March 29, 1983
INVENTOR(S) : David W. Suobank et al It is certified that error appears in the above-identified patent and that said Letters Patent are hereby corrected as shown below:

Column 6, line 1, change "it" to --its--.

Column 7, lines 65 and 66, correct "occurrence".

Column 8, line 5, change "low-chart" to --flow-chart--.

Column 9, line 6, omit "are" first occurrence.

line 27, correct "preceding".

line 40, omit "the" first occurrence.

Column 10, line 11, correct "occurring".

line 17, correct "occurring".

line 58, correct "position".

Column 14, line 48, change "accordance" to --association--.

Signed and Sealed this

Thirty-first Day of May 1983

[SEAL]

Attest:

DONALD J. QUIGG

Attesting Officer     Acting Commissioner of Patents and Trademarks